United States Patent [19]

Mullane

[11] Patent Number: 4,742,076

[45] Date of Patent: May 3, 1988

[54] ETODOLAC FOR LOWERING RHEUMATOID FACTOR

[75] Inventor: John F. Mullane, Westchester, N.Y.

[73] Assignee: American Home Products Corporation, New York, N.Y.

[21] Appl. No.: 57,462

[22] Filed: Jun. 3, 1987

[51] Int. Cl.$^4$ ............................................. A61K 31/40
[52] U.S. Cl. .................................................... 514/411
[58] Field of Search ......................................... 514/411

[56] References Cited

U.S. PATENT DOCUMENTS

| | | | |
|---|---|---|---|
| 4,533,551 | 8/1985 | Martel | 514/411 |
| 4,670,462 | 6/1987 | Hatz et al. | 514/411 |
| 4,677,132 | 6/1987 | Hayward | 514/411 |

OTHER PUBLICATIONS

Chem. Abst. 101-222257g (1984).
J. S. Goodwin et al, "Administration of Nonsteroidal Anti-Inflammatory Agents in Patients With Rheumatoid Arthritis", JAMA, vol. 250, No. 16, pp. 2485-2488 (1983).
Forre, O. et al, Non-Steroidal Anti-Inflammatory Drugs in Rheumatoid Arthritis" Inflammation, Supplement to vol. 8, 1984.
Pope, R. M. et al, "Differential Effects of Therapeutic Regiments on Specific Classes of Rheumatoid Factor", Ann. Rheum. Dis. 1986; 45; 183-189.

*Primary Examiner*—Stanley J. Friedman
*Attorney, Agent, or Firm*—John W. Routh

[57] ABSTRACT

A method is disclosed for lowering rheumatoid factor blood levels by administering an effective amount of etodolac.

3 Claims, No Drawings

ETODOLAC FOR LOWERING RHEUMATOID FACTOR

BACKGROUND OF THE INVENTION (a) Field of the Invention

This invention relates to a novel therapeutic use of 1,8-diethyl-1,3,4,9-tetrahydropyrano[3,4-b]indole-1-acetic acid whose generic name is etodolac. More specifically this invention relates to a method for lowering rheumatoid factor blood levels in humans for treatment of rheumatoid arthritis.

(b) Prior Art

The active agent of this invention, 1,8-diethyl-1,3,4,9-tetrahydropyrano[3,4-b]indole-1-acetic acid or a therapeutically acceptable salt thereof, is disclosed in U.S. Pat. No. 3,939,178 issued Feb. 17, 1976. This active agent, hereinafter designated by its generic name etodolac, previously has been reported to be useful as an analgesic and anti-inflammatory agent. (See U.S. Pat. No. 3,939,178).

Rheumatoid factors of the IgM, IgA and IgG classes have been detected in the circulation and are produced locally by the synovium of patients with adult onset rheumatoid arthritis. James S. Goodwin et al in an article entitled "Administration of Nonsteroidal Anti-inflammatory Agents in Patients With Rheumatoid Arthritis" in JAMA, Vol. 250, No. 16, pages 2485-2488 (1983) describes a study wherein pirioxicam was substituted, after two weeks of placebo therapy, in 20 patients who had previously been taking various nonsteroidal anti-inflammatory drugs. The serum rheumatoid factor levels rose when placebo was substituted for the previous drug and piroxicam administration was associated with a fall in rheumatoid factor levels to approximately 62% of the baseline level. I have now unexpectedly that etodolac, either in its free acid form or in its therapeutically acceptable salt form, is useful for lowering rheumatoid factor blood levels in humans, and particularly humans suffering from arthritis.

This finding, coupled with the fact that etodolac is a relatively safe drug, renders the method of this invention particularly useful and advantageous.

SUMMARY OF THE INVENTION

According to this invention a method is provided for lowering rheumatoid factor blood levels in a human in need of said treatment, which comprises administering to the human an effective amount of etodolac, or a therapeutically acceptable salt thereof.

DETAILS OF THE INVENTION

According to the present method, etodolac, either in its free acid form or in the therapeutically acceptable salt form, is employed as the active agent. Examples of suitable salt forms are described in U.S. Pat. No. 3,939,178 and include the sodium, potassium, magnesium, triethylamine and benzylamine salt forms. A preferred salt form is the sodium salt, i.e. etodolac sodium.

Etodolac or a therapeutically acceptable addition salt thereof is administered to humans suffering from elevated rheumatoid factor blood levels, either orally or parenterally. For many reasons oral administration is preferred.

While etodolac or a therapeutivally acceptable salt thereof can be administered alone, e.g. as a sole component of a filled capsule, it is preferred to formulate the compound in various dosage forms for oral or parenteral administration, e.g. tablets, or sterile solutions. Such formulations are described in U.S. Pat. No. 3,939,178, herein incorporated by reference in its entirety.

When utilizing etodolac or one of its above-noted salts as agents for lowering rheumatoid factor blood levels, the total dose of active agent can range from about 50 milligrams to about 1000 milligrams per day with a preferred dosage range of from 200 to 600 milligrams per day. However, greater lowering of rheumatoid factor can be achieved with 1000 mg per day. Generally, a parenteral dose or an oral dose is administered in one to four applications per day, but more commonly twice a day. Such doses are considered to be an effective amount when, following their administration, a decrease in rheumatoid factor blood levels is experienced by the patient, or when the subjective symptoms complained of by said human beings are reported as having disappeared, or as being ameliorated or reduced in severity following such treatment.

The effectiveness of etodolac or its therapeutically acceptable salts as agents for lowering rheumatoid factor blood levels in a human has been demonstrated in human patients.

Six-month and one year double-blind, randomized multicenter studies were conducted with patients having active documented rheumatoid arthritis of duration of at least one year but not more than 7 years with at least 6 tender or painful joints on motion, at least 3 swollen joints, greater than 45 minutes of morning stiffness, a history of joint pain, and a Westergren sedimentation rate of at least 30 mm/hr. Patients were randomly assigned to one of three treatment groups as follows:

| Group | Drug | Dosage |
| --- | --- | --- |
| I | Etodolac | 300 mg/day |
| II | Etodolac | 1000 mg/day |
| III | Ibuprofen | 2400 mg/day |

The patients first underwent a screening visit followed within three weeks by a baseline visit. The safety baseline visit was scheduled to allow sufficient time for washout of any previously taken non-steroidal anti-inflammatory drug, flare of rheumatoid arthritis disease activity, and review of screening laboratory data. All patients took medication 4 times a day at 7 AM, Noon, 5 PM and 10 PM. Group I and Group II patients took divided doses of medication at 7 AM and 10 PM and placebo at noon and 5 PM. Group III patients took medication 4 times a day.

Maintenance visits were scheduled for two week intervals at first and then extending to 4 and 8 week intervals, 10 visits being scheduled during the first six months and 16 visits being schedule during the year. At each visit, laboratory tests including tests for rheumatoid factor were performed. The rheumatoid factor test was accomplished by means of a nephelometric immunassay. The results are shown in the table below:

|  | Etodolac 150 mg bid | Etodolac 500 mg bid | Ibuprofen 600 mg qid |
| --- | --- | --- | --- |
| Six Months |  |  |  |
| Number of patients | 150 | 97 | 110 |
| Value (IU/ml) |  |  |  |
| Baseline | 858.7 | 890.0 | 790.2 |
| 6 month | 836.9 | 785.3 | 811.3 |

|  | Etodolac 150 mg bid | Etodolac 500 mg bid | Ibuprofen 600 mg qid |
|---|---|---|---|
| difference One Year | −21.8 | −104.7 | +21.1 |
| Number of patients | 92 | 59 | 65 |
| Value (IU/ml) | | | |
| Baseline | 833.9 | 928.0 | 911.1 |
| 1 year | 736.2 | 771.3 | 1067.4 |
| difference | −97.7 | −157.7 | +156.3 |

In the course of reviewing these data it was observed that serum rheumatoid factor progressively improves with etodolac treatment in a dose related manner but not with ibuprofen.

The serum of patients with rheumatoid arthritis contain antibodies specific for IgG (rheumatoid factors). Since immunological mechanisms play a role in rheumatoid arthritis, it is beneficial that rheumatoid factor levels decrease in the presence of etodolac. It also is known that patients with high titres of IgG tend to have more severe disease and thus poorer prognosis.

The method of this invention is particularly beneficial for lowering rheumatoid factor blood levels in a patient suffering from rheumatoid arthritis. The lowering of the rheumatoid factor blood levels was in addition to the usual anti-inflammatory effect exhibited by etodolac.

It has been hypothesized that inhibition of rheumatoid factor production in vivo, by interfering with the disease process at a more proximal step in rheumatoid inflammation, may be a previously unrecognized mode of action of these drugs in patients with rheumatoid arthritis.

In any event, it has been demonstrated that etodolac caused a significant reduction in levels of total rheumatoid factor in the blood and indicates that etodolac suppresses rheumatoid factor production and effects immune reactions at the disease sites of inflammation. This contrasts with the data on ibuprofen which actually shows an increase in rheumatoid factor over the course of treatment suggesting that inhibition of rheumatoid factor is empirical for any particular anti-inflammatory agent.

I claim:

1. A method for lowering rheumatoid factor blood levels in a human in need of treatment for rheumatoid arthritis, which comprises administering to the human an effective amount of etodolac or a therapeutically acceptable salt thereof.

2. The method of claim 1 in which the effective amount of etodolac is within the range of from about 50 mg to about 1000 mg per day.

3. The method of claim 1 in which the effective amount of etodolac is within the range of 200 mg to 1000 mg per day.

* * * * *